United States Patent
Cai et al.

(10) Patent No.: US 12,038,421 B2
(45) Date of Patent: Jul. 16, 2024

(54) METHOD FOR RAPIDLY DETERMINING GRADE OF BLACK TEA

(71) Applicant: Anhui Agricultural University, Hefei (CN)

(72) Inventors: Huimei Cai, Hefei (CN); Mengying Shuai, Hefei (CN); Xiaochun Wan, Hefei (CN); Daxiang Li, Hefei (CN); Chuanyi Peng, Hefei (CN)

(73) Assignee: Anhui Agricultural University, Hefei (CN)

(*) Notice: Subject to any disclaimer, the term of this patent is extended or adjusted under 35 U.S.C. 154(b) by 276 days.

(21) Appl. No.: 17/690,205

(22) Filed: Mar. 9, 2022

(65) Prior Publication Data

US 2022/0291181 A1   Sep. 15, 2022

(30) Foreign Application Priority Data

Mar. 10, 2021   (CN) .......................... 202110259651.2

(51) Int. Cl.
| | |
|---|---|
| *G01N 30/86* | (2006.01) |
| *G01N 30/30* | (2006.01) |
| *G01N 33/14* | (2006.01) |
| *G01N 30/02* | (2006.01) |

(52) U.S. Cl.
CPC ......... *G01N 30/8693* (2013.01); *G01N 30/30* (2013.01); *G01N 30/8675* (2013.01); *G01N 33/14* (2013.01); *G01N 2030/027* (2013.01)

(58) Field of Classification Search
None
See application file for complete search history.

(56) References Cited

FOREIGN PATENT DOCUMENTS

| CN | 103018384 A | * | 4/2013 | |
|---|---|---|---|---|
| CN | 103028384 A | * | 4/2013 | |
| CN | 104914190 A | * | 9/2015 | |
| CN | 108205042 A | * | 6/2018 | ............. G01N 30/02 |
| CN | 108760870 A | * | 11/2018 | ............. G01N 27/62 |

(Continued)

OTHER PUBLICATIONS

Chen, Q. et al., "Identification of Green Tea's (*Camellia sinensis* (L.)) Quality Level According to Measurement of Main Catechins and Caffeine Contents by HPLC and Support Vector Classification Pattern Recognition", Journal of Pharmaceutical and Biomedical Analysis, vol. 48, 2008, pp. 1321-1325.*

(Continued)

*Primary Examiner* — Daniel S Larkin

(57) ABSTRACT

A method for determining a grade of black tea by HPLC detection belongs to the field of tea grade determination. The specific steps are as follows: adding known black tea powder samples of different grades into boiling water of 95-100° ° C. for extraction, and filtering with a filter membrane with a pore size in a range of 0.20-0.25 um to obtain black tea sample liquid; measuring contents of ten components by peak area normalization method; standardizing data of the contents of the ten components in a black tea sample solution; carrying out unsupervised principal component analysis; carrying out supervised partial least squares discriminant analysis; carrying out hierarchical clustering analysis on the basis of partial least squares discriminant analysis, and finally establishing a tea grade discrimination model based on HPLC.

4 Claims, 11 Drawing Sheets

(56) References Cited

FOREIGN PATENT DOCUMENTS

| CN | 110832317 A | * | 2/2020 | ............. G01N 30/02 |
| CN | 113884593 A | * | 1/2022 | ............. G01N 30/02 |
| JP | 2009014700 A | * | 1/2009 | |
| JP | 5177384 B2 | * | 4/2013 | |
| WO | WO-2018227384 A1 | * | 12/2018 | ............. G01N 30/02 |

OTHER PUBLICATIONS

Gu, Hui-Wen et al., "Differentiating Grades of Xihu Longjing Teas According to the Contents of Ten Major Components Based on HPLC-DAD in Combination with Chemometrics", LWT—Food Science and Technology, vol. 130, 2020, 109688, pp. 1-8.*

Huang, J. et al., "Qualitative Discrimination of Chinese Dianhong Black Tea Grades Based on a Handheld Spectroscopy System Coupled with Chemometrics", Food Science and Nutrition, vol. 8, 2020, pp. 2015-2024.*

Sharma, A. et al., "Chemometric Assisted RP-HPLC for Fingerprinting of Indian Orthodox Black Tea", Analytical Methods, vol. 6, 2014, pp. 2189-2196.*

* cited by examiner

| Grade of Keemun Factory No.2 Black Tea mg/g | | | | | | | |
|---|---|---|---|---|---|---|---|
| Component | QM2-Special grade | QM2-1 | QM2-2 | QM2-3 | QM2-4 | QM2-5 | QM2-6 |
| Theobromine | 17.5±0.1 | 17.0±0.1 | 16.3±0.3 | 15.1±0.3 | 13.6±1.4 | 13.8±2.2 | 13.9±0.4 |
| EGC | 7.2±0.0 | 7.3±0.0 | 7.2±0.0 | 6.7±0.1 | 6.4±0.4 | 6.6±0.5 | 6.9±0.2 |
| Theine | 50.1±0.2 | 48.2±0.5 | 48.4±0.8 | 46.1±0.7 | 40.8±3.6 | 40.5±6.8 | 41.8±1.2 |
| EC | 1.4±0.0 | 1.7±0.0 | 1.8±0.0 | 1.5±0.1 | 1.3±0.2 | 1.6±0.3 | 1.6±0.2 |
| EGCG | 14.1±0.0 | 14.1±0.1 | 14.7±0.3 | 13.7±0.3 | 12.1±0.7 | 12.9±1.5 | 11.4±0.5 |
| ECG | 1.7±0.0 | 1.6±0.0 | 1.6±0.0 | 1.3±0.0 | 1.1±0.1 | 1.2±0.2 | 1.1±0.1 |
| TF1 | 2.3±0.0 | 2.4±0.0 | 2.4±0.0 | 2.4±0.0 | 2.4±0.0 | 2.4±0.1 | 2.4±0.0 |
| TF3 | 2.1±0.0 | 2.0±0.0 | 2.0±0.0 | 2.0±0.0 | 2.0±0.0 | 2.0±0.1 | 2.0±0.0 |
| TF2A | 1.9±0.0 | 1.9±0.0 | 1.9±0.0 | 1.9±0.0 | 1.8±0.0 | 1.8±0.1 | 1.9±0.0 |
| TF2B | 1.8±0.0 | 1.8±0.0 | 1.9±0.1 | 1.8±0.0 | 1.8±0.0 | 1.8±0.0 | 1.8±0.0 |

| Grade of Tanyang black tea mg/g | | | | |
|---|---|---|---|---|
| Component | TY-Special grade | TY-Grade I | TY-Grade II | TY-Grade III |
| Theobromine | 19.7±0.7 | 18.8±0.7 | 14.7±0.5 | 12.6±0.1 |
| EGC | 10.3±0.3 | 9.7±0.3 | 9.5±0.3 | 8.9±0.1 |
| Theine | 48.8±1.6 | 47.7±1.6 | 47.5±1.9 | 47.1±0.1 |
| EC | 1.4±0.1 | 1.5±0.1 | 1.5±0.1 | 1.5±0.1 |
| EGCG | 12.9±0.3 | 13.7±0.3 | 13.4±0.5 | 12.5±0.1 |
| ECG | 1.2±0.1 | 1.2±0.1 | 1.3±0.1 | 1.2±0.0 |
| TF1 | 2.2±0.0 | 2.2±0.0 | 2.2±0.0 | 2.2±0.0 |
| TF3 | 1.7±0.0 | 1.8±0.0 | 1.8±0.0 | 1.8±0.0 |
| TF2A | 1.7±0.0 | 1.7±0.0 | 1.7±0.0 | 1.7±0.0 |
| TF2B | 2.0±0.0 | 2.0±0.1 | 2.0±0.1 | 2.0±0.0 |

FIG. 12B

| Grade of Sichuan Leshan black tea mg/g | | | |
|---|---|---|---|
| Component | YPH | HMD | MJH |
| Theobromine | 60.8.±0.5 | 32.7±0.4 | 26.9±0.7 |
| EGC | 9.2±0.6 | 10.6±0.7 | 11.0±0.3 |
| Theine | 53.4±0.3 | 54.1±0.3 | 53.4±0.3 |
| EC | 3.8±0.4 | 2.8±0.5 | 3.6±0.3 |
| EGCG | 26.4±0.9 | 22.5±0.5 | 18.7±0.7 |
| ECG | 6.2±0.2 | 3.6±0.1 | 3.7±0.3 |
| TF1 | 2.3±0.0 | 2.7±0.0 | 2.3±0.0 |
| TF3 | 2.1±0.0 | 2.6±0.0 | 2.0±0.0 |
| TF2A | 2.1±0.0 | 2.4±0.0 | 1.8±0.0 |
| TF2B | 3.0±0.0 | 3.2±0.0 | 2.1±0.0 |

FIG. 12C

METHOD FOR RAPIDLY DETERMINING GRADE OF BLACK TEA

CROSS-REFERENCE TO RELATED APPLICATION

This application claims priority to Chinese Patent Application No. 202110259651.2, filed on Mar. 10, 2021, the contents of which are hereby incorporated by reference in its entirety.

TECHNICAL FIELD

The application belongs to the technical field of determining black tea grade, and in particular to a method for rapidly determining a grade of black tea based on high-performance liquid chromatography (HPLC).

BACKGROUND

Tea is one of the four major beverages in the world originating from China. Drinking tea is not only a leisurely way of life, but also a good way of health care. Polyphenol compounds, powerful antioxidants contained richly in tea, can effectively scavenge harmful free radicals produced by human body, slow down tissue ageing and reduce the incidence of cardiovascular diseases. Generally there are three types of tea: green tea (non-fermented), oolong tea (semi-fermented) and black tea (fermented). Catechins and theaflavins are the main polyphenols in black tea and they are the indicator polyphenols for evaluating the quality of black tea. The content of catechin, the most abundant polyphenol in tea, in black tea is usually lower than that in green tea, for catechins are oxidized and polymerized during fermentation when tea leaves are manufactured; however, a high content of theaflavins is present in black tea because black tea is fully fermented. For black tea, the main non-volatile components are polyphenols and alkaloids (thein and theobromine), and the grade determination of black tea is inextricably linked with the content of these polyphenols and alkaloids. The demand for quality black tea has been increasing as people's living standards have gradually improved. Due to insufficient market regulation and the profit motive of the merchants, the market for premium tea is often characterized by substandard black tea, which seriously damages the interests of consumers and has a negative impact on the development of tea culture in China. In determining the quality of black tea, manual sensory evaluation is often used to assess the quality of black tea, but the results are easily influenced by the physiological and psychological state of the evaluator and the evaluation environment, making it difficult to meet the current requirements for accuracy and repeatability in tea quality testing.

Various analytical methods based on differences in the intrinsic composition of tea leaves have been proposed to avoid the subjectivity of sensory evaluation. Compared with traditional sensory analysis, chemical analysis techniques could provide more objective and more accurate results. Previous studies have found that differences in tea grades between different production areas or origins largely depend on the content of major components and mineral elements, but for different grades of tea from the same production area, the content of major components is similar and only a few characteristic components vary from one another. Therefore, the characteristic components can be used to reduce the chemical index of the actual tea quality analysis, so as to reduce testing costs and testing duration, and improve the analytical accuracy of the corresponding model. HPLC allows the separation and identification of substance components, which is mainly done by separating and identifying non-volatile components in black tea for qualitative and quantitative analysis, thus enabling the identification of tea quality grades. However, tea quality is determined by a number of factors jointly, so the quantitative and comprehensive comparison of tea bioactive components by HPLC, followed by multivariate analysis software to find the main differential substances of different grades of black tea and qualitative analysis, provides a new way for tea grading and classifying, and is of significant importance for identifying tea quality grades.

SUMMARY

An objective of the application is to provide a method for rapidly determining grades of black teas, and the method may be simple, sensitive, efficient, etc.

In order to achieve the above objective, the present application adopts the following technical scheme:

1. preparing HPLC standard stock solutions: ten standard products, including four kinds of catechins (namely epigallocatechin (EGC), epicatechin (EC), epigallocatechin gallate (ECG) and epicatechin gallate (EGCG)), four kinds of theaflavins (namely theaflavins (TF1), theaflavins-3-gallate (TF2A), theaflavins-3-gallate (TF2B) and theaflavins-bis-gallate (TF3)), theobromine and thein; accurately weighing 10 mg of each of the ten substances above, quickly putting it into a 5 mL centrifugal tube and diluting it with distilled water to obtain a standard stock solution with a concentration of 2 mg/mL, and placing it at $-40°$ C. for later use;

2. preparing standard solutions: preparing theobromine and thein, EC, ECG at 60, 80, 100, 120 (unit in mg/L), preparing EGC, EGCG, TF1 TF2A TF2B and TF3 at 120, 180, 200 and 240 (unit in mg/L); then using a 0.22 μm (pore size) organic system microporous filter membrane for filtration, followed by HPLC detection to plot standard curves;

3. preparing samples: weighing 0.2 g (accurate to 0.001 g) of evenly ground black tea powder sample into a centrifugal tube, adding 10 mL of distilled water at 80° C., mixing evenly, immediately moving the tube into boiling water at 95-100° C. for extraction for 10 min, performing stirring once every 3-5 min, then letting it cool to room temperature after leaching, and performing centrifugation; taking the supernatant and filtering it with a filter membrane with a pore size in a range of 0.20-0.25 μm, and storing the filtrate in refrigerator at 4° C. for later use;

4. determining tea fractions by HPLC, where a mobile phase is acetonitrile and ultrapure water at a flow rate of 0.6-1.0 mL/min and contents are measured by peak area normalization;

5. importing data into a multivariate analysis software (such as SIMCA, SPSS, MetaboAnalyst, MassProfiler Professional), standardizing the data and then performing unsupervised principal component analysis, which makes the classification result more objective without pre-classification; then performing a supervised partial least squares discriminant analysis to obtain more accurate results by amplifying differences between groups while shrinking/narrowing a difference within each group, and to obtain relevant data such as contribution margin and predictive power, with cumulative predictive power values ($Q^2$) and cumulative variance contribution margin (R2Y) close to 1.0 indicating a good model; further, carrying out hierarchical cluster analysis on the basis of partial least squares discriminant analysis, where the hierarchical cluster analysis is based on the nature of subjects to realize classification, distances corresponding to large and small differences in nature respectively are far and near, it can be seen directly that the cluster analysis gives a re-grading diagram of different grades of different kinds of black teas, an importance factor (VIP) value in the partial least squares discriminant analysis quantifies the contribution of each variable to the classification, and a VIP value larger than 1 indicates that the variable differs significantly between different classes of black teas in different grades; and finally, developing a model for establishing tea grade differentiation model based on HPLC;

6. steps in the algorithm of principal component analysis (1) standardization of original index data (also referred to as original indicator data)

setting n numbers of samples and p numbers of indicators, and obtaining a data matrix $X=(x_{ij})_{n \times p}$, $i=1, 2, \ldots, n$ stands for the n numbers of samples, $j=1, 2, \ldots, p$; p represents the p numbers of indicators, $x_{ij}$ is the $j^{th}$ index value of the $i^{th}$ sample;

(2) data standardized transformation of data with Z-score method: $Z_{ij}=(x_{ij}-x_j)/S_j$ (3) finding the correlation matrix of index data: $R=(r_{jk})_{p \times p}$, $j=1, 2, \ldots, k=1, 2, \ldots, p$; $r_{jk}$ is the correlation coefficient between index j and index k;

(4) finding eigenvectors of eigenvalues of the correlation matrix R to determine principal components: obtaining the p numbers of characteristic roots (eigenvalues) $\lambda_g$ (g=1, 2, \ldots, p) from the characteristic equation $|\lambda I_p - R| = 0$, ranking $\lambda_g$ in order of magnitude as $\lambda_1 \geq \lambda_2 \geq \ldots \geq \lambda_p \geq 0$, wherein $\lambda_g$ is the variance of the principal components, and its magnitude describes the role of each principal component in describing the evaluated object; according to the characteristic equation, corresponding each characteristic root to a characteristic vector $L_g$ ($L_g = l_{g1}, l_{g2}, \ldots, l_{gp}$), g=1, 2, \ldots, p; transforming the standardized index variables into principal components: $Fg = l_{g1}Z_1 + l_{g2}Z_2 + \ldots + l_{gp}Z_p$ (g=1, 2, \ldots, p), wherein $F_1$ is called as first principal component, $F_2$ is called as the second principal component, \ldots, and $F_p$ is called as the $p^{th}$ principal component;

(5) finding the variance contribution rate and determining the number of principal components: generally, the number of principal components is equal to the number of original indicators; if there are many original indicators, comprehensive evaluation will be more troublesome, the principal component analysis is to select as few k principal components (k<p) as possible for comprehensive evaluation while still keeping the amount of information lost as low as possible;

7. steps in the algorithm for partial least squares discriminant analysis (1) modeling method: setting up n numbers of samples, with q numbers of dependent variables and p numbers of independent variables; forming data tables X and Y for the independent and dependent variables; using partial least squares regression to extract t and u from X and Y respectively, with t and u carrying as much information as possible about the variance in their respective data tables, and t and u being correlated to the maximum extent possible; after the first component has been extracted, implementing the partial least squares regression for X on t and for Y on t, respectively; if the regression equation has reached satisfactory accuracy, the algorithm terminates; otherwise, a second round of component extraction is performed using the residual information from the interpretation of X by t and the residual information from the interpretation of Y by t. This is repeated until a more satisfactory accuracy can be achieved; if multiple components in total are eventually extracted for X, the partial least squares regression will be performed by imposing a regression of yk on these components of X, which will then be expressed as a regression equation of yk on the original independent variables;

(2) marking the data matrix obtained by X after standardization as $E_0 = (E_{01}, E_{0p})n \times p$ and the matrix corresponding to Y as $F_0 = (F_{01}, \ldots, F_{0q})n \times q$; noting that $t_1$ is the first component of $E_0$, $t_1 = E_{0w1}$, $w_1$ is the first axis of $E_0$ and it is a unit vector, i.e. $\|w_1\|=1$; marking $u_1$ as the first component of $F_0$, $u_1 = F_{0c1}$, $c_1$ is the first axis of $F_0$, and $\|c_1\|=1$; then, solving the following optimization problem, i.e., noting that $\theta_1 = w_1'E_0'F_{0c1}$, which is precisely the objective function value of the optimization problem; using Lagrange algorithm, obtaining $E_0'F_0F_0'E_{0w1} = \theta_{12}w_1$ and $F_0'E_0E_0'F_{0c1} = \theta_{12}c_1$; therefore, $w_1$ is the unit eigenvector corresponding to the maximum eigenvalue of $E_0'F_0F_0'E_0$ matrix, and $c_1$ is the unit eigenvector corresponding to the maximum eigenvalue $\theta_{12}$ of $F_0'E_0E_0'F_0$ matrix; the components $t_1 = E_{0w1}$ and $u_1 = F_{0c1}$ can be obtained after finding the axes $w_1$ and $c_1$; then, finding the regression equations: $E_0 = t_1p_1' + E_1$, $F_0 = t_1r_1' + F_1$ of $E_0$ and $F_0$ on $t_1$ respectively, wherein the regression coefficient vectors are $p_1 = E_0't_1/\|t_1\|_2$; $r_1 = F_0't_1/\|t_1\|_2$; and $E_1$ and $F_1$ are residual matrices of the two equations respectively; and (3) replacing $E_0$ and $F_0$ with residual matrices $E_1$ and $F_1$, and then finding the second axes $w_2$ and $c_2$ and the second components $t_2$ and $u_2$, where $t_2 = E_1w_2$, $u_2 = F_1c_2$, $\theta_2 = <t_2, u_2> = w_2'E_1'F_1c_2$; $w_2$ is the unit eigenvector corresponding to the maximum eigenvalue of $E_1'F_1F_1'E_1$ matrix, while $c_2$ is the unit eigenvector corresponding to the maximum eigenvalue $\theta_{22}$ of $F_1'E_1E_1'F_1$ matrix; calculating the regression coefficient $p_2 = E_1't_2/\|t_2\|2$; $r_2 = F_1't_2/\|t_2\|2$; therefore, there are regression equations $E_1 = t_2p_2' + E_2$, $F_1 = t_2r_2' + F_2$; in this way, if the rank of X is A, then $E_0 = t_1p_1' + \ldots + tA_{pA}'$; $F_0 = t_1r_1' + \ldots + tArA' + FA$;

(4) cross-validity: one more component is worthwhile if a prediction error sum of squares (all dependent variables and predicted samples combined) in case for one more component and one less sample divided by an error sum of squares (all dependent variables and samples combined) in case for one less component is less than 0.952.

Beneficial Effects

The application provides a method for rapidly determining a grade of black tea by HPLC combined with chemometrics analysis. The method creatively uses ten standard products, namely four kinds of catechins (EGC, EC, ECG and EGCG), four kinds of theaflavins (TF1, TF2A, TF2B and TF3), theobromine and thein. The method can enable accurate classification of different grades of black teas, thus solving the problem of grading tea leaves solely by artificial experience. In this method, data is used to grade tea leaves, and the grading result can meet the requirements of the national standard for tea grading; the method may be rapid, simple, sensitive, efficient, and the like, and allow the grading of different types of black tea regardless of the variety of black tea. For the first time, a digital standard for black tea grading has also been established, the standardization and modernization of tea production and harvesting could hence be promoted.

BRIEF DESCRIPTION OF THE DRAWINGS

FIGS. 11A-11D illustrate standard curves II of different substances.

FIGS. 12A-12C show the contents of catechins, purine alkaloids and theaflavins in different grades of black teas.

DETAILED DESCRIPTION OF EMBODIMENTS

For a better understanding of the technical features, objectives and beneficial effects of the present application, a further description of the application is given below in connection with specific embodiments, but the application is not limited to the present embodiments.

In all the embodiments of the application, the tea grade is determined according to the Chinese national standard (GB/T 23776-2009).

Tanyang Gongfu black tea (Special-grade: 1, 2, 3; Grade I: 4, 5, 6; Grade II: 7, 8, 9; Grade III: 10, 11, 12; Grade IV: 13, 14, 15);

Keemun black tea (Special-grade: 1, 2, 3; Grade I: 4, 5, 6; Grade II: 7, 8, 9; Grade III: 10, 11, 12; Grade IV: 13, 14, 15; Grade V: 16, 17, 18; Grade VI: 19, 20, 21);

Sichuan Leshan black tea (Special-grade: 1, 2, 3; Grade I: 4, 5, 6; Grade II: 7, 8, 9).

Embodiment 1

Figure 1:
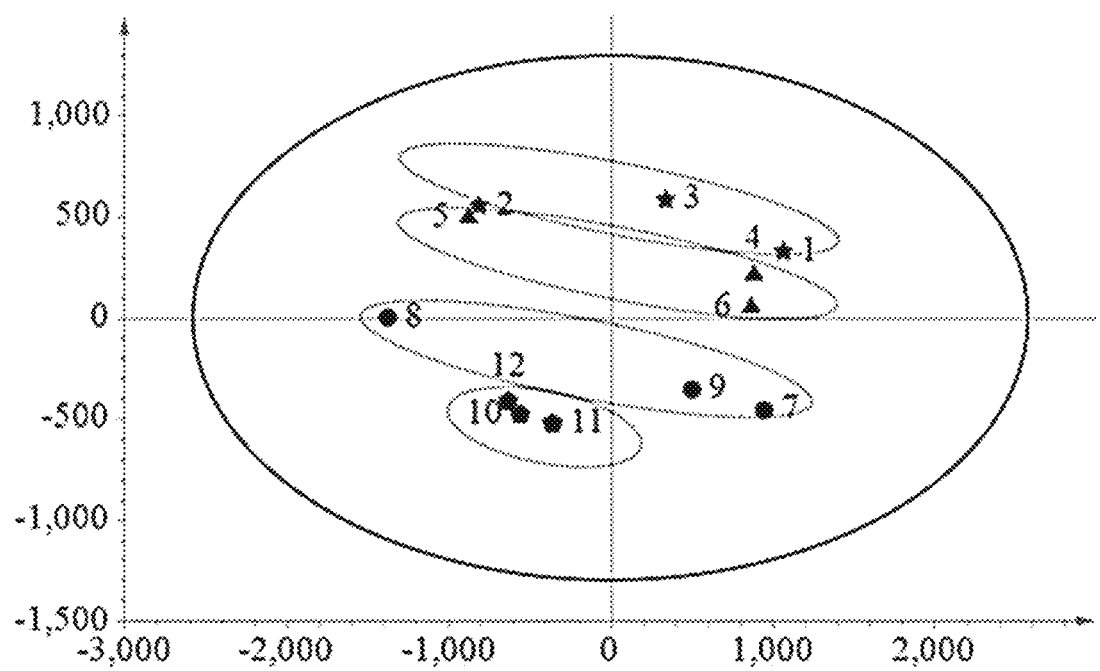
FIG. 1 illustrates the principal component analysis of Tanyang Gongfu black tea (R2X=0.948, $Q^2$=0.995).
Figure 2:
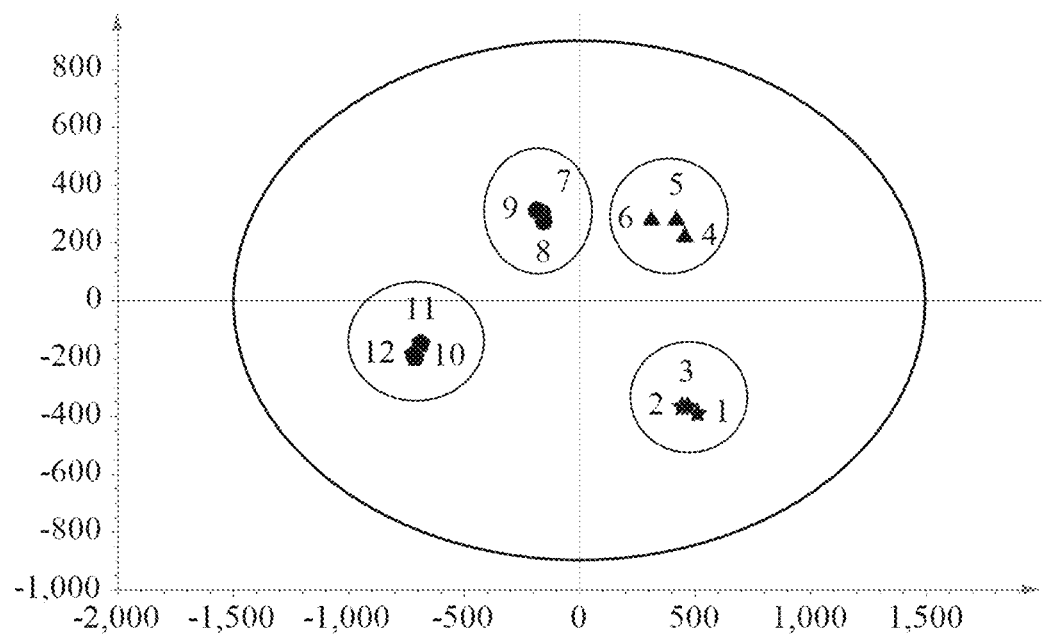
FIG. 2 shows the partial least squares discriminant analysis of Tanyang Gongfu black tea (R2Y=0.975, $Q^2$=0.899).
Figure 3:
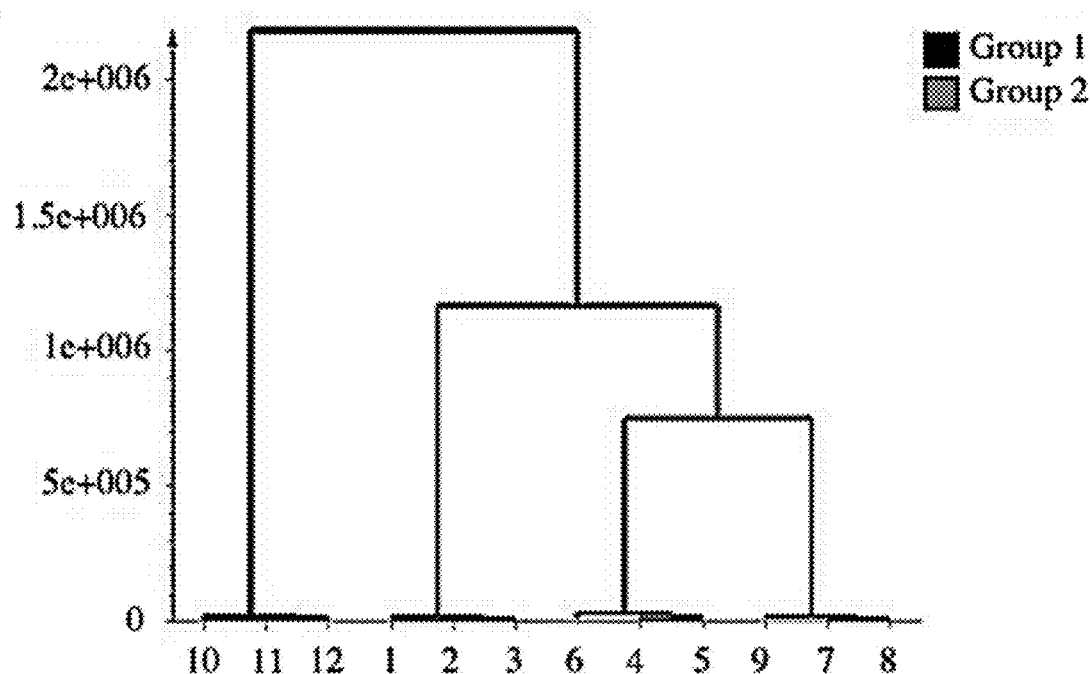
FIG. 3 shows the hierarchical cluster analysis of Tanyang Gongfu black tea.

Weighing 0.200 g of evenly ground Tanyang Gongfu black tea powder sample into a centrifuge tube, adding 10 mL of distilled water at 80° ° C., mixing evenly, immediately moving into boiling water at 95-100° C. for extraction for 10 min, performing stirring once every 3-5 min, letting it cool to room temperature after leaching, and performing centrifugation; taking the supernatant and performing filtration by a filter membrane with pore size of 0.20 um and putting the filtrate into a liquid vial; using HPLC to separate and identify the components of tea, where the mobile phase is acetonitrile and ultrapure water with a flow rate of 0.6-1.0 mL/min and the peak area normalization method is used to measure the content; importing the data into SIMCA software, standardizing the data and performing unsupervised principal component analysis, which makes the classification result more objective without pre-classification, and the principal component analysis result of Tanyang Gongfu black tea is illustrated in FIG. 1; then, carrying out supervised partial least squares discriminant analysis; obtaining rather accurate results by enlarging the differences between groups and reducing the differences within groups, and obtaining relevant data such as contribution rate and predictive ability, with cumulative predictive power values (Q2) and cumulative variance contribution margin (R2Y) close to 1.0 indicating a good model, and the partial least squares discriminant analysis result of Tanyang Gongfu black tea is illustrated in FIG. 2; further, carrying out hierarchical cluster analysis on the basis of partial least squares discriminant analysis, where the hierarchical cluster analysis is based on the nature of subjects to be classified, the distance corresponding to a large and small difference in nature is far and near, it could be seen directly that the cluster analysis gives a re-grading diagram of different grades of different kinds of black tea, value of VIP in partial least squares discriminant analysis quantifies the contribution of each variable to the classification, and a VIP value larger than 1 indicates that the variables differ significantly between different classes of black tea in different grades, and the hierarchical cluster analysis result of Tanyang Gongfu black tea is illustrated in FIG. 3; and finally, developing a model for establishing tea grade differentiation based on HPLC; the VIP values show that theobromine, theine and EGC can be used to classify Tanyanggong black tea into Special-grade, Grade I, Grade II and Grade III, and the contents of EGC, EC, ECG, EGCG, TF1, TF2A, TF2B, TF3, theobromine and theine in different grades of Tanyang Gongfu black tea are illustrated in FIG. 12B; the results are consistent with those determined by GB/T 23776-2009, proving that this method to grade black tea is accurate and valid.

Importing the data into the multivariate analysis software SPSS, standardizing the data and then performing unsupervised principal component analysis, which makes the classification result more objective without pre-classification; then carrying out supervised partial least squares discriminant analysis; obtaining rather accurate results by enlarging the differences between groups and reducing the differences within groups, and obtaining relevant data such as contribution rate and predictive ability, with cumulative predictive ability ($Q^2$) and cumulative variance contribution rate (R2Y) close to 1.0 indicating a good model; further, carrying out hierarchical clustering analysis based on the partial least squares discriminant analysis, where hierarchical clustering analysis is to classify subjects according to their properties, and the distance between the large and small properties is far and near; it can be seen directly that clustering analysis gives the re-classification charts of different grades and different kinds of black tea; the VIP values in partial least squares discriminant analysis could be used to quantify the contribution of each variable to classification, with VIP value greater than 1 indicating that there are significant differences among different types and grades of black tea; finally, developing a tea grade discrimination model based on HPLC.

Among them the data standardization and unsupervised principal component analysis methods of the multivariate analysis software are as follows:

(1) standardization of original index data setting up n numbers of samples and p numbers of indicators (also referred to as indexes), obtaining the available data matrix $X=(x_{ij})_{n \times p}$, i=1, 2, . . . , n represents n numbers of samples, j=1, 2, . . . , p; p represents p numbers of indicators, $x_{ij}$ stands for the $j^{th}$ index value of the $i^{th}$ sample;

(2) standardized transformation of the data with Z-score method: $Z_{ij}=(x_{ij}-x_j)/S_j$ (3) finding the correlation matrix of index data: $R=(r_{jk})_{p \times p}$, j=1, 2, . . . , k=1, 2, . . . , p; $r_{jk}$ is the correlation coefficient between index j and index k.

(4) finding the eigenvectors of the eigenvalues of the correlation matrix R to determine the principal components: obtaining the p numbers of characteristic roots $\lambda_g$ (g=1, 2, . . . , p) from the characteristic equation $|\lambda_{Ip}-R|=0$, ranking $\lambda_g$ in order of magnitude as $\lambda_1 \geq \lambda_2 \geq \ldots \geq \lambda_p \geq 0$, where $\lambda_g$ is the variance of principal component, and its magnitude describes the role of each principal component in describing the evaluated object; according to the characteristic equation, corresponding each characteristic root to a characteristic vector $L_g$ ($L_g=lg_1, lg_2, \ldots, l_{gp}$), g=1, 2, p; transforming the standardized index variables into principal components: $F_g = l_{g1}Z_1 + l_{g2}Z_2 + \ldots + l_{gp}Z_p$ (g=1, 2, . . . , p), where $F_1$ is called as first principal component, $F_2$ is called as second principal component, . . . , and $F_p$ is called as $p^{th}$ principal component;

(5) finding the variance contribution rate and determining the number of principal components: generally the number of principal components is equal to the number of original indicators; if there are many original indicators, comprehensive evaluation will be more troublesome, the principal component analysis is to select as few k principal components (k<p) as possible for comprehensive evaluation while still keeping the amount of information lost as low as possible.

The steps in the algorithm for partial least squares discriminant analysis are as follows:

(1) modeling method: setting up n numbers of samples, with q numbers of dependent variables and p numbers of independent variables; forming data tables X and Y for the independent and dependent variables; using partial least squares regression to extract t and u from X and Y respectively, with t and u carrying as much information as possible about the variance in their respective data tables, and t and u being correlated to the maximum extent possible; after the first component has been extracted, implementing the partial least squares regression for X on t and for Y on t, respectively; if the regression equation has reached satisfactory accuracy, the algorithm terminates; otherwise, a second round of component extraction is performed using the residual information from the interpretation of X by t and the residual information from the interpretation of Y by t. This is repeated until a more satisfactory accuracy can be achieved; if multiple components in total are eventually extracted for X, the partial least squares regression will be performed by imposing a regression of yk on these components of X, which will then be expressed as a regression equation of yk on the original independent variable;

(2) marking the data matrix obtained by X after standardization as $E_0 = (E_{01}, E_{0p})_{n \times p}$ and the matrix corresponding to Y as $F_0 = (F_{01}, \ldots, F_{0q})$ n×q; noting that $t_1$ is the first component of $E_0$, $t_1 = E_{0w1}$, $w_1$ is the first axis of $E_0$ and it is a unit vector, i.e. $\|w_1\|=1$; marking $u_1$ as the first component of $F_0$, $u_1 = F_{0c1}$, $c_1$ is the first axis of $E_0$, and $\|c_1\|=1$; then, solving the following optimization problem, i.e., noting that $\theta_1 = w_1'E_0'F_{0c1}$, which is precisely the value of the objective function of the optimization problem; using Lagrange algorithm, obtaining $E_0'F_0F_0'E_{0w1} = \theta_{12}w_1$ and $F_0'E_0E_0'F_{0c1} = \theta_{12}c_1$; therefore, $w_1$ is the unit eigenvector corresponding to the maximum eigenvalue of $E_0'F_0F_0'E_0$ matrix, and $c_1$ is the unit eigenvector corresponding to the maximum eigenvalue $\theta_{12}$ of $F_0'E_0E_0'F_0$ matrix; the components $t_1 = E_{0w1}$ and $u_1 = F_{0c1}$ can be obtained after finding the axes $w_1$ and $c_1$; then, finding the regression equations: $E_0 = t_1p_1' + E_1$, $F_0 = t_1r_1' + F_1$ of $E_0$ and $F_0$ on $t_1$ respectively, wherein the regression coefficient vectors are $p_1 = E_0't_1/\|r_1\|_2$; $r_1 = F_0't_1/\|t_1\|_2$; and $E_1$ and $F_1$ are residual matrices of the two equations respectively; and (3) replacing $E_0$ and $F_0$ with residual matrices $E_1$ and $F_1$, and then finding the second axes $w_2$ and $c_2$ and the second components $t_2$ and $u_2$, where $t_2 = E_1w_2$, $u_2 = F_1c_2$, $\theta_2 = <t_2$, $u_2> = w_2E_1'F_1c_2$; $w_2$ is the unit eigenvector corresponding to the maximum eigenvalue of $E_1'F_1F_1'E_1$ matrix, while $c_2$ is the unit eigenvector corresponding to the maximum eigenvalue $\theta_{22}$ of $F_1'E_1E_1'F_1$ matrix; calculating the regression coefficient $P_2 = E_1't_2/\|t_2\|2r_2 = F_1't_2/\|t_2\|2$; therefore, there are regression equations $E_1 = t_2p_2 + E_2$, $F_1 = t_2r_2' + F_2$; in this way, if the rank of X is A, then $E_0 = t_1p_1' + \ldots + tA_{pA}'$; $F_0 = t_1r_1' + \ldots + tArA' + FA$;

(4) cross-validity: one more component is worthwhile if a prediction error sum of squares (all dependent variables and predicted samples combined) in case for one more component and one less sample divided by an error sum of squares (all dependent variables and samples combined) in case for one less component is less than 0.952.

Embodiment 2

Figure 4:
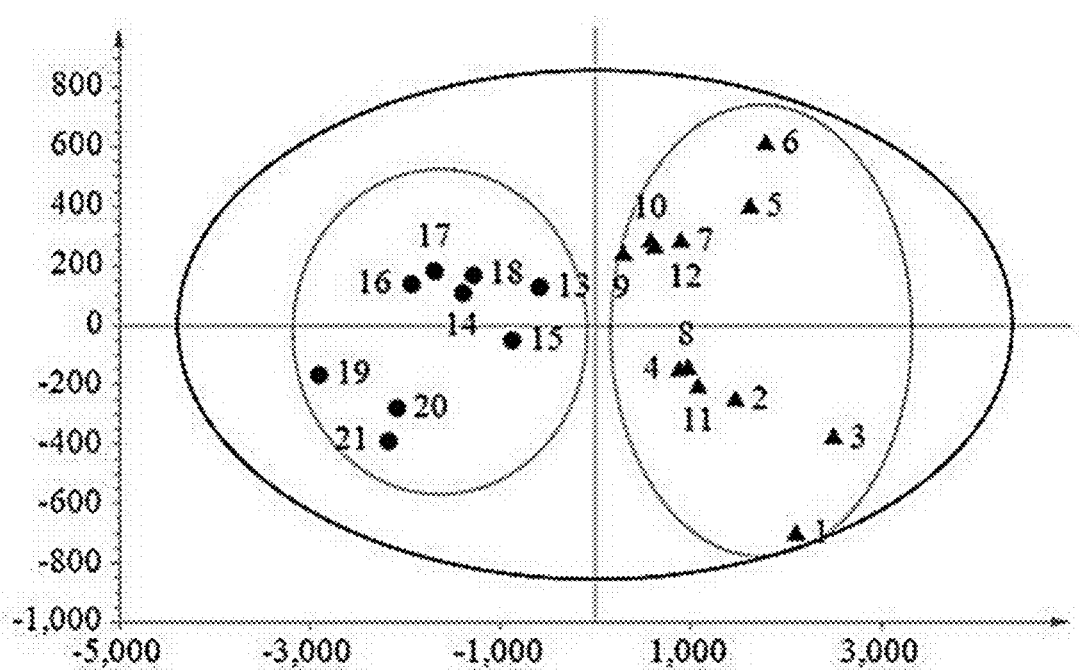
FIG. 4 illustrates the principal component analysis of Keemun black tea (R2X=0.916, $Q^2$=0.805).
Figure 5:
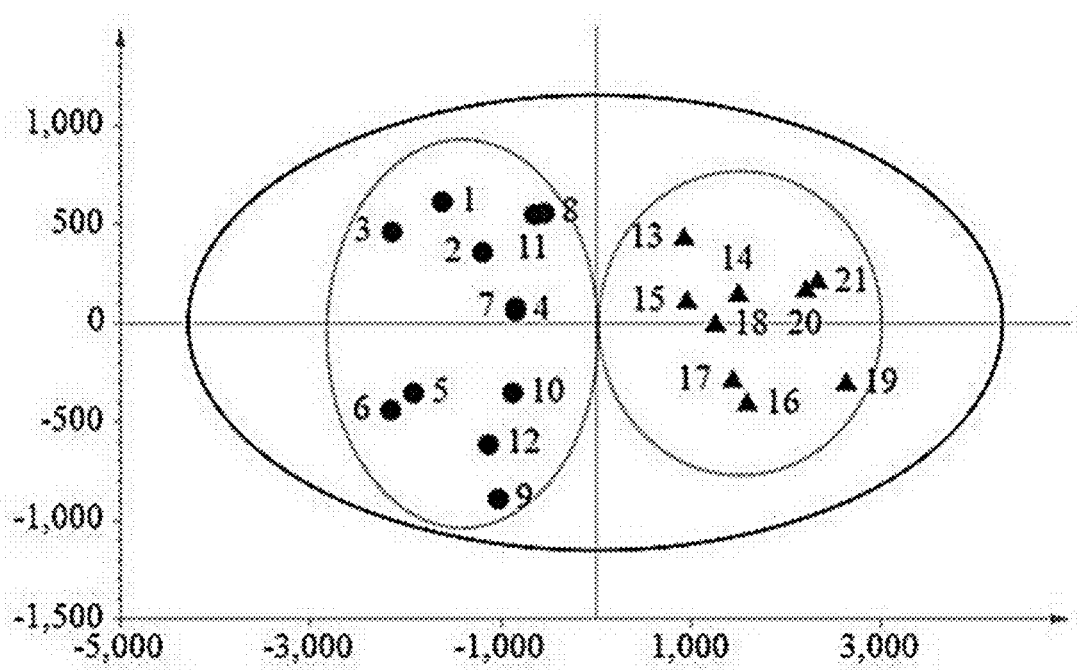
FIG. 5 shows the partial least squares discriminant analysis of Keemun black tea (R2Y=0.885, $Q^2$=0.799).
Figure 6:
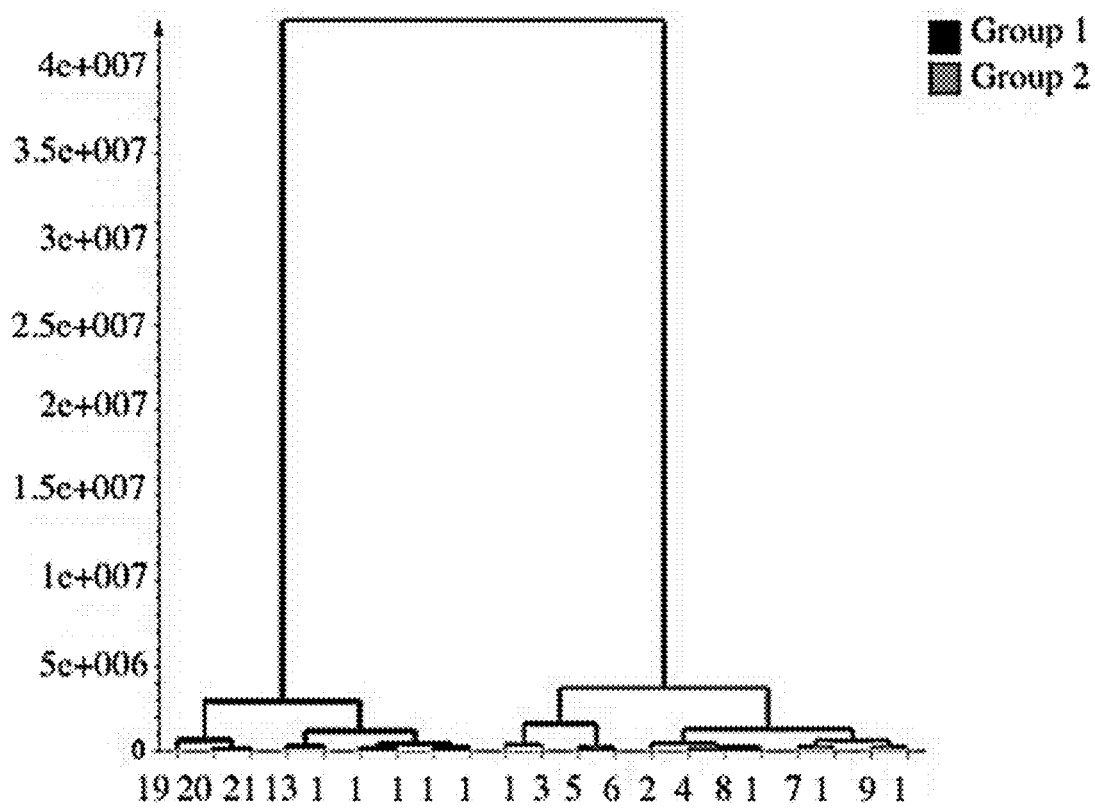
FIG. 6 shows the hierarchical cluster analysis of Keemun black tea.
Figure 11A:
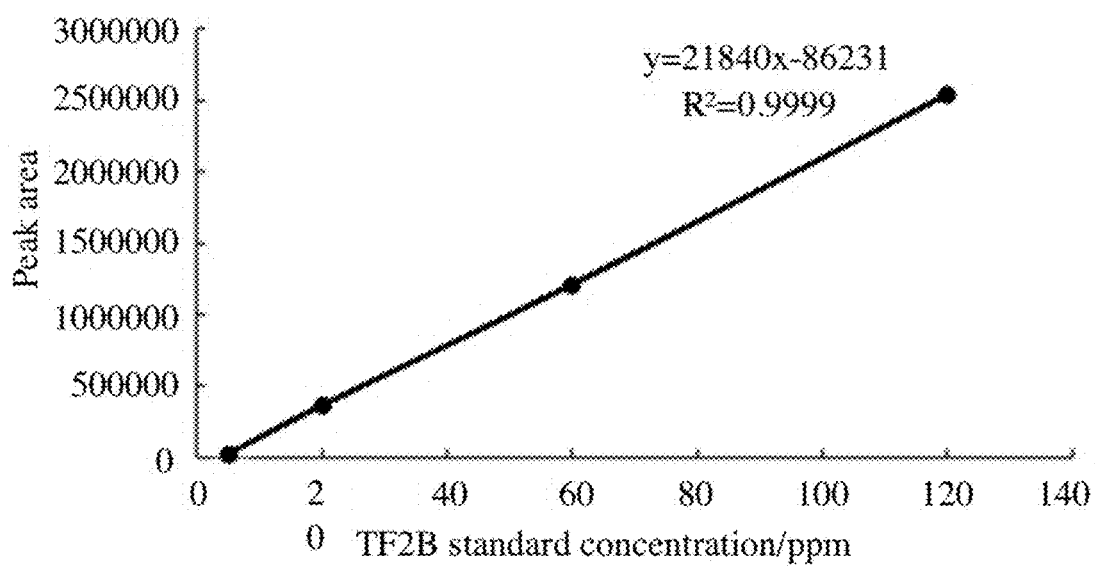
Figure 11B:
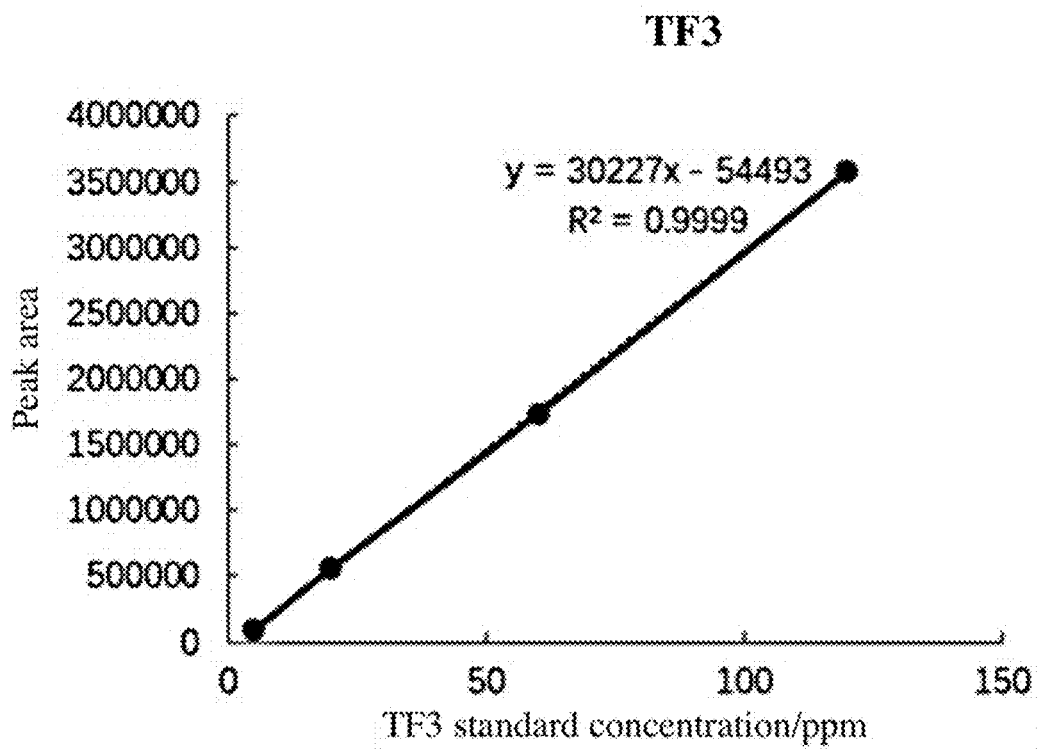
Figure 11C:
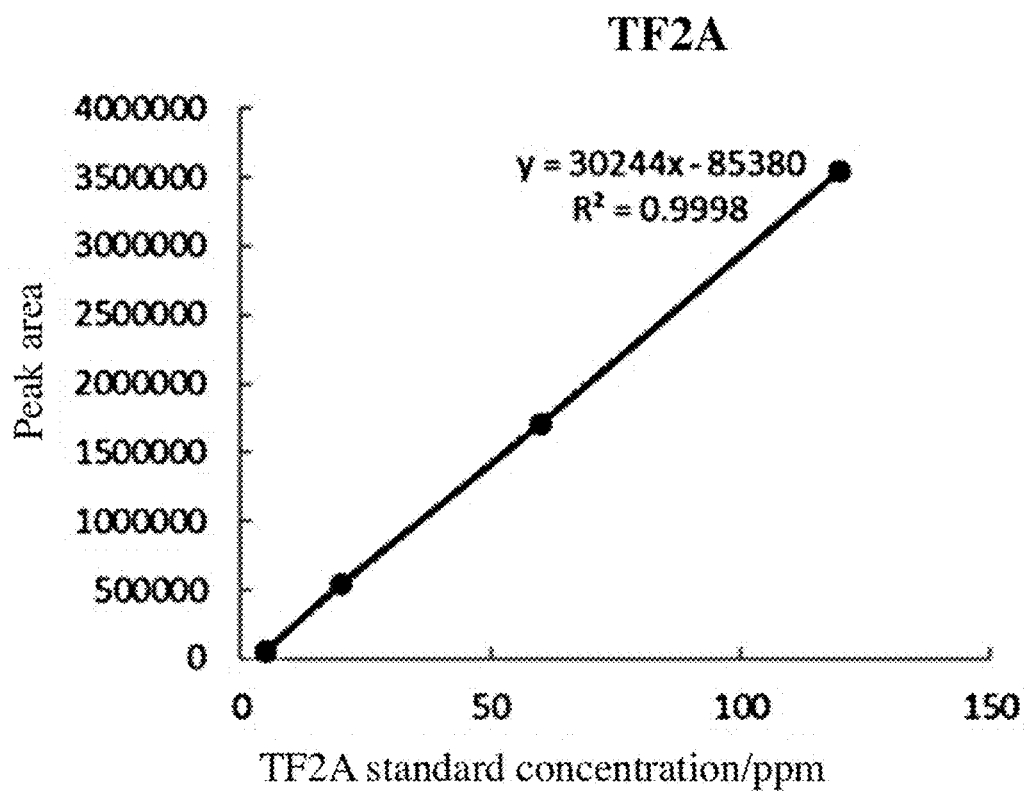
Figures 11D, 12A:
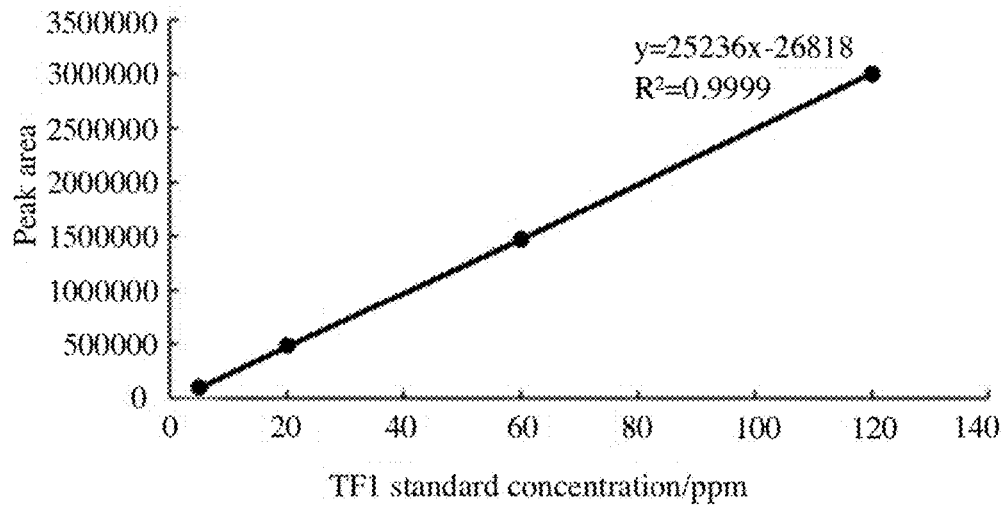

Weighing 0.200 g of evenly ground Keemun black tea powder sample into a centrifugal tube, adding 10 mL of distilled water at 80° C., mixing well, immediately moving the tube into boiling water at 95-100° ° C.for extraction for 10 min, performing stirring once every 3-5 min, letting it cool to room temperature after leaching, followed by centrifugation; taking the supernatant and performing filtration with a filter membrane with pore size of 0.22 um, then, putting the filtrate into a liquid vial; using HPLC to separate and identify the components of tea, wherein the mobile phase is acetonitrile and ultrapure water, the flow rate is 0.6-1.0 mL/min, and the content is measured by peak area normalization method; importing the data into SIMCA software, standardizing the data and performing unsupervised principal component analysis, which makes the classification result more objective without pre-classification, the principal component analysis result of Keemun black tea is illustrated in FIG. 4; then, carrying out supervised partial least squares discriminant analysis, obtaining rather accurate results by enlarging the differences between groups and reducing the differences within groups, and obtaining relevant data such as contribution rate and predictive ability, with the cumulative predictive ability (Q2) and cumulative variance contribution rate (R2Y) close to 1.0 indicating a good model, the partial least squares discriminant analysis result of Keemun black tea is illustrated in FIG. 5; further, carrying out hierarchical clustering analysis based on the partial least squares discriminant analysis, wherein hierarchical clustering analysis is to classify subjects according to their properties, and the distance between the large and small properties is far and near; it can be seen directly that clustering analysis gives the re-classification charts of different grades and different kinds of black tea; the VIP values in partial least squares discriminant analysis can be used to quantify the contribution of each variable to classification, with VIP value greater than 1 indicating that there are significant differences among different types and grades of black tea, and the hierarchical cluster analysis result of Keemun black tea is illustrated in FIG. 6; finally, developing a tea grade discrimination model based on HPLC, wherein the VIP value shows that theine and ECG can be used to classify Keemun black tea into high grade (Special-grade, Grade I, Grade II and Grade III) and low grade (Grade IV, Grade V and Grade VI) and the contents of the EGC, EC, ECG, EGCG, TF1, TF2A, TF2B, TF3, theobromine and theine in different grades of Keemun black tea are illustrated in FIG. 12A; the results are consistent with those determined by GB/T23776-2009, proving that this method for grading black tea is accurate and effective.

Among them, the data standardization of the multivariate analysis software, the unsupervised principal component analysis method and the algorithm of the partial least squares discriminant analysis are the same as those in Embodiment 1.

Embodiment 3

Figure 7:
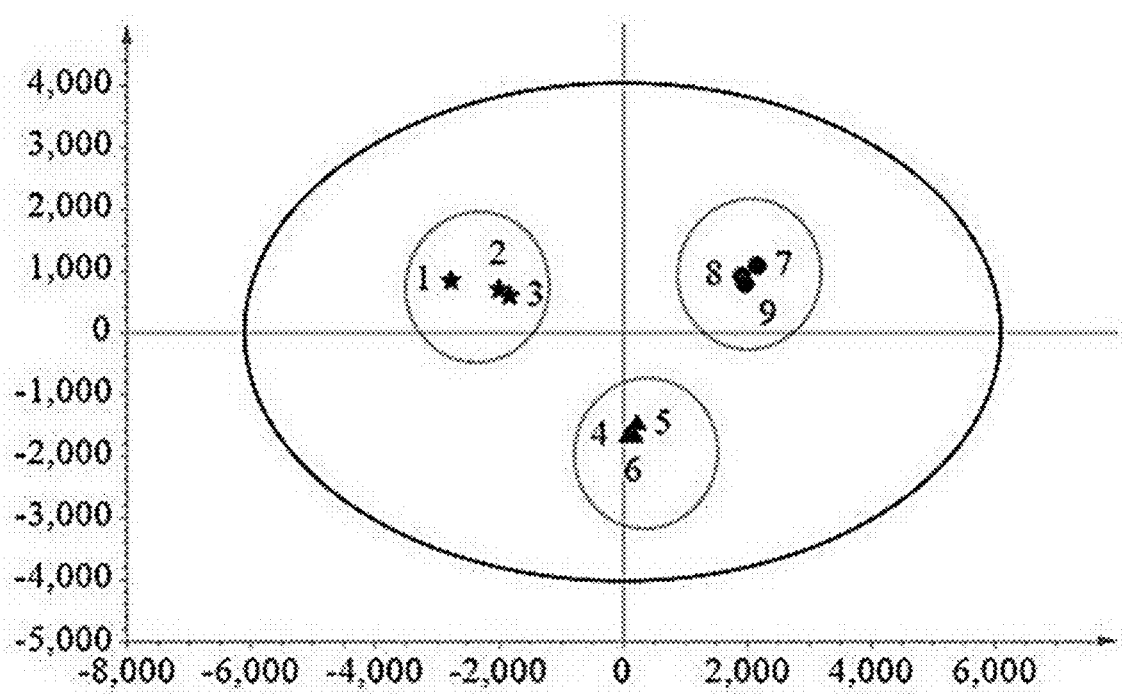
FIG. 7 illustrates principal component analysis of Sichuan Leshan black tea (R2 X=0.999, $Q^2$=0.985).
Figure 8:
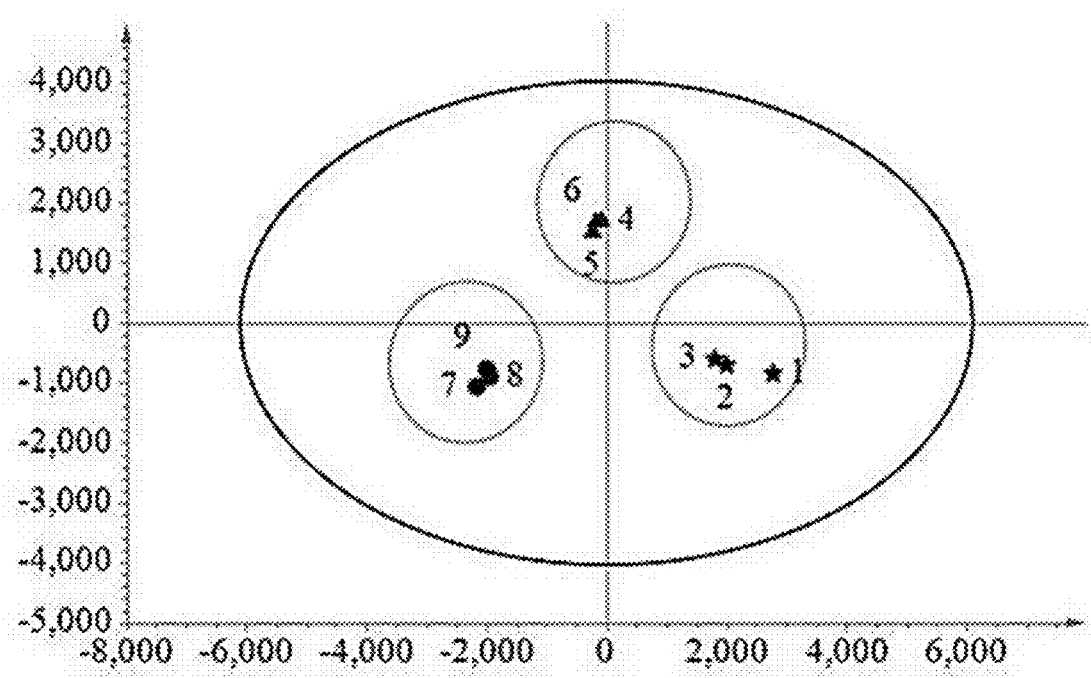
FIG. 8 shows the partial least squares discriminant analysis of Sichuan Leshan black tea (R2 Y=0.986, $Q^2$=0.975).
Figure 9:
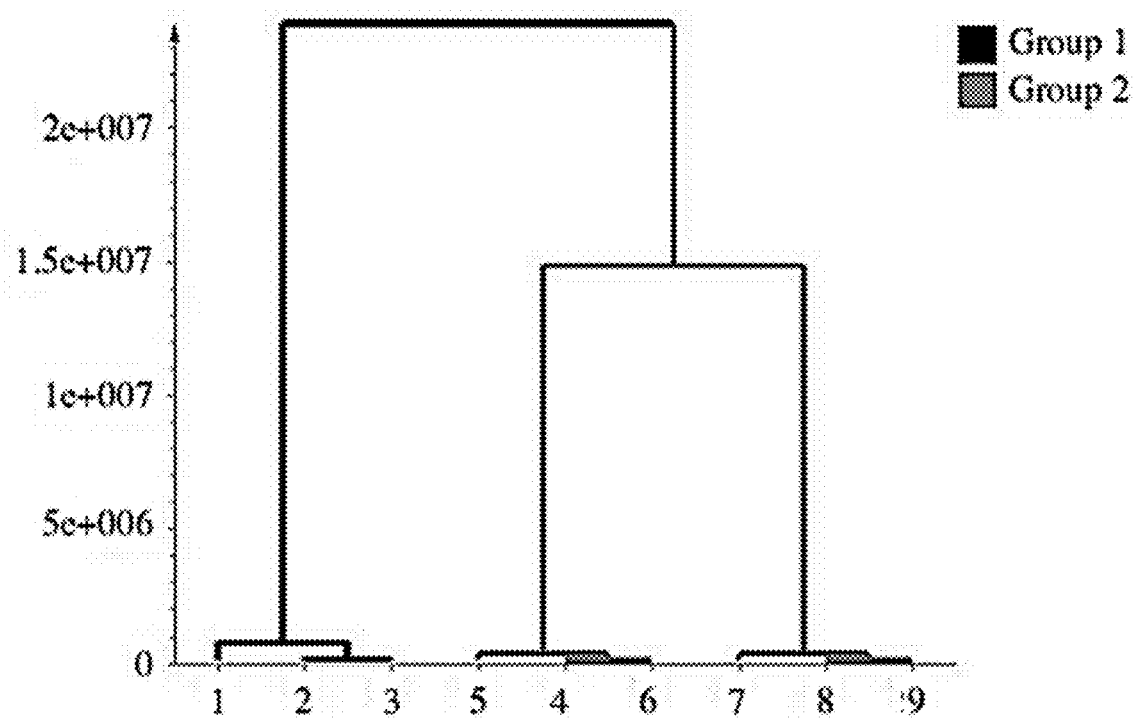
FIG. 9 shows the hierarchical cluster analysis of Sichuan Leshan black tea.
Figure 10A:
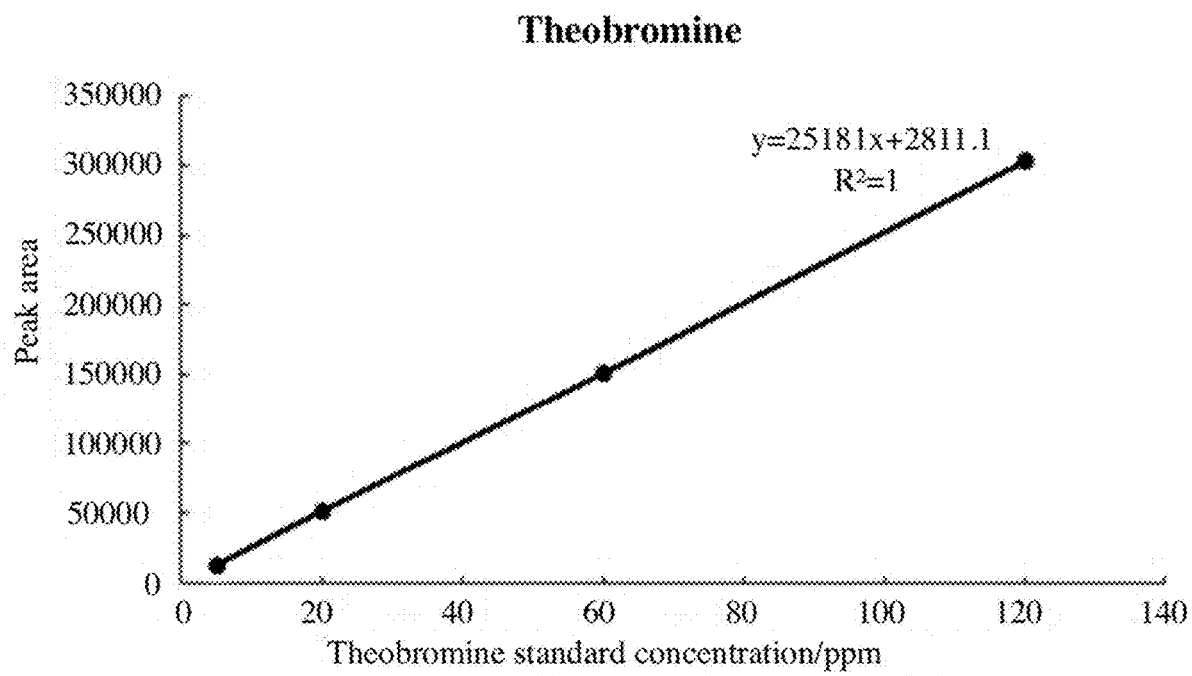
FIGS. 10A-10F illustrate standard curves I of different substances.
Figure 10B:
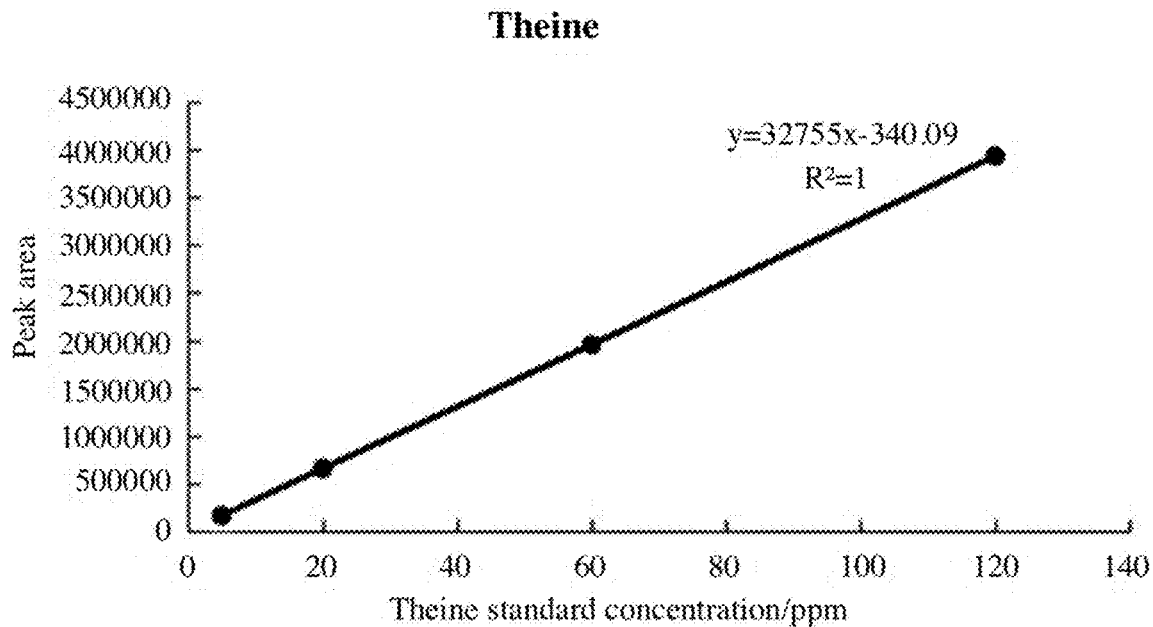
Figure 10C:
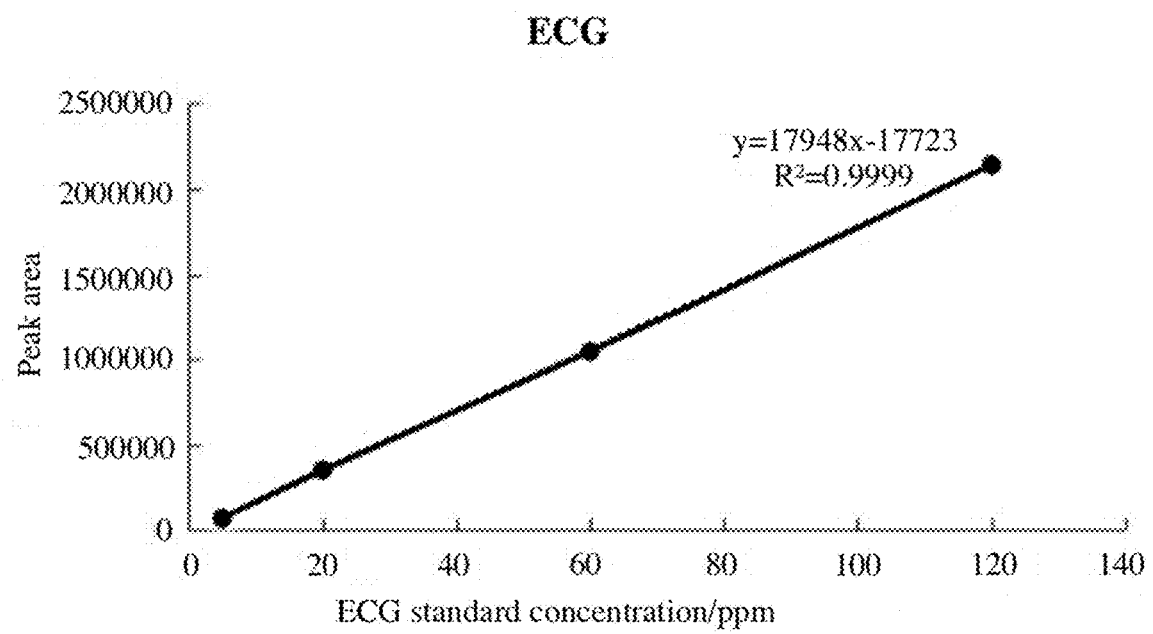
Figure 10D:
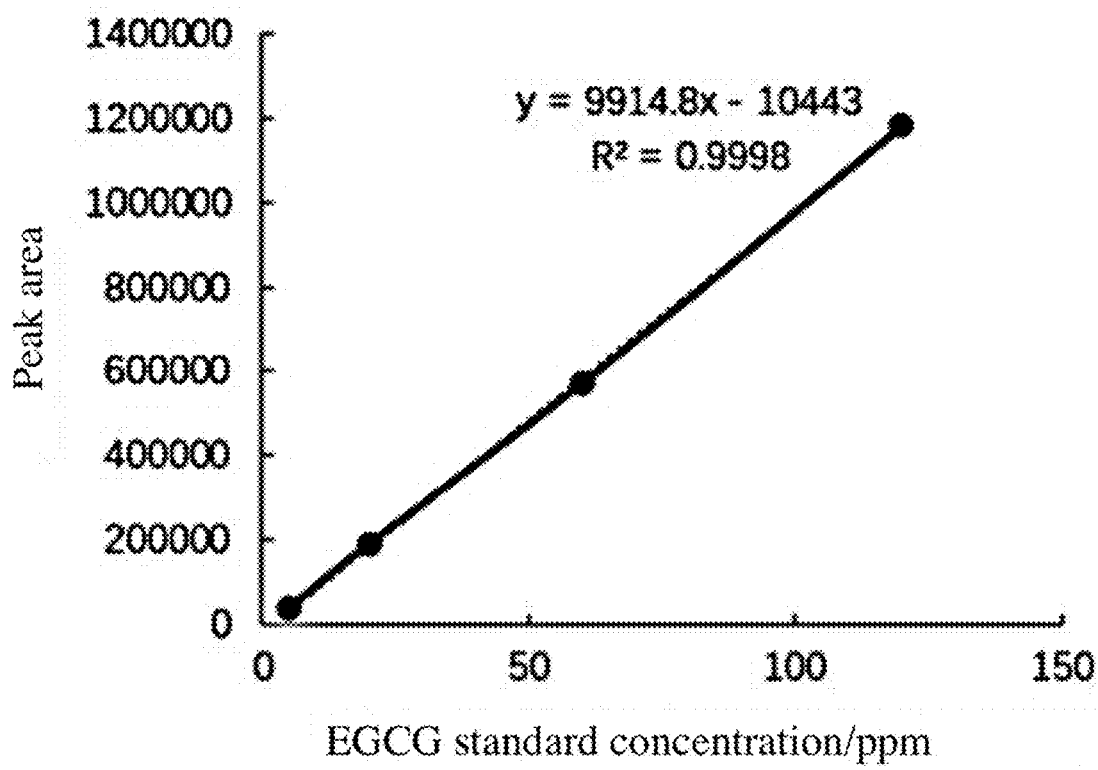
Figure 10E:
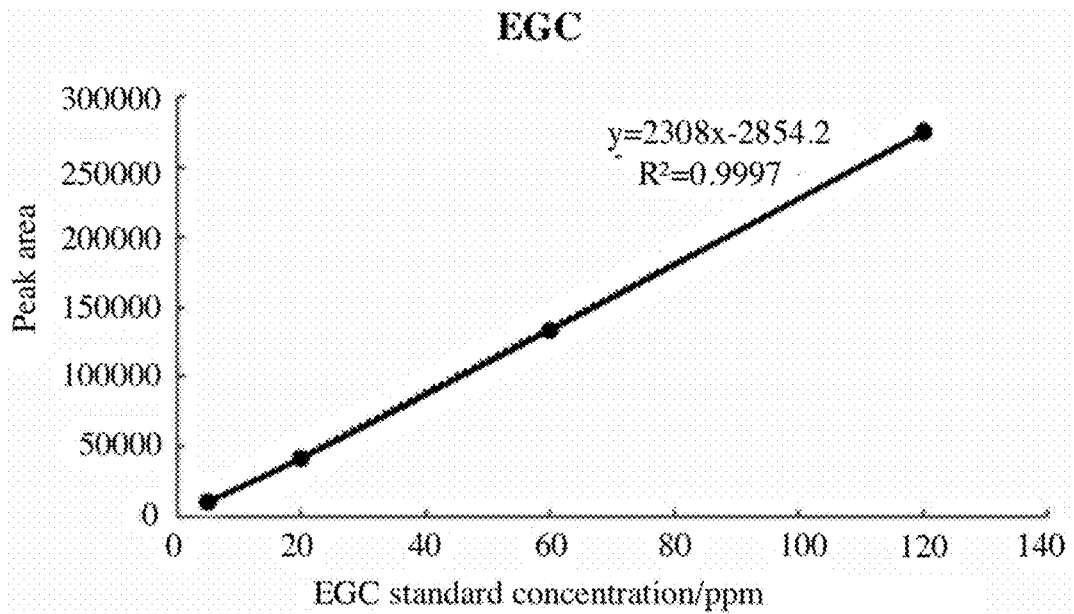
Figure 10F:
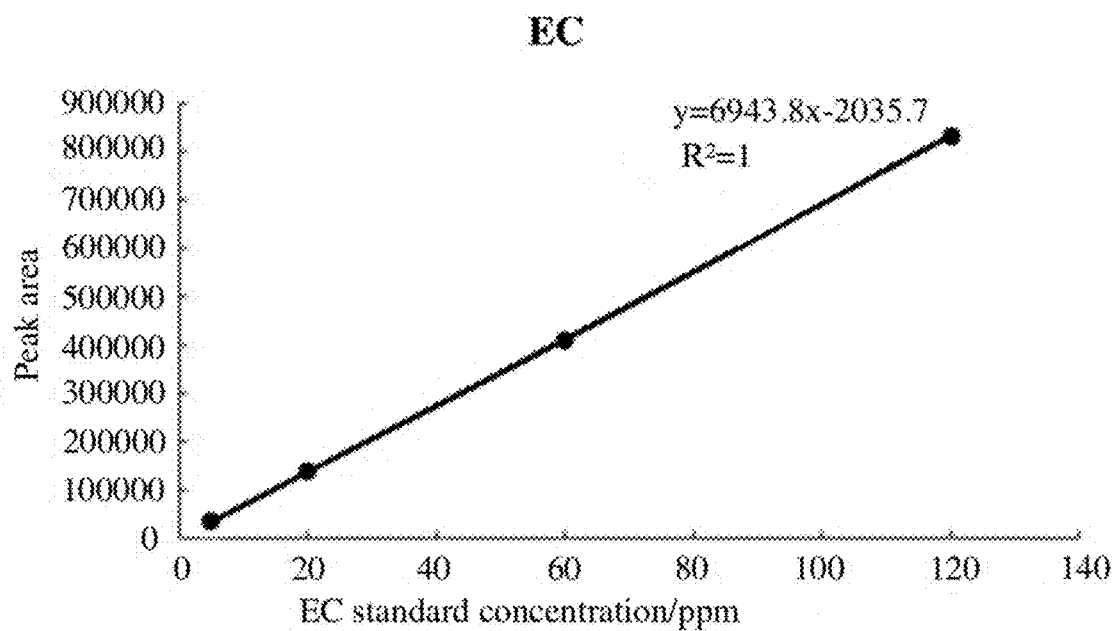

Weighing 0.200 g of evenly ground Sichuan Leshan black tea powder sample into a centrifuge tube, adding 10 mL of distilled water at 80° ° C., mixing well, immediately moving the tube into boiling water at 95-100° C. for extraction for 10 min, performing stirring once every 3-5 min, letting it cool to room temperature after leaching, followed by centrifugation; taking the supernatant which is subjected to filtration by a filter membrane with pore size of 0.25 um, then putting the filtrate into a liquid vial, and separating and identify the components of tea by HPLC, wherein the mobile phase A is ultrapure water, mobile phase B is 1% formic acid, mobile phase C is acetonitrile, the flow rate is 0.8 mL/min, the elution duration is 70 min, the ultraviolet detection wavelength is 280 nm, and the column temperature is 30° C.; substituting the peak area into the standard curve to measure the content of the compound, and the standard curves I of the theobromine, theine, ECG, EGCG, EGC, and EC are respectively illustrated in FIGS. 10A to 10F and the standard curves II of the TF2B, TF3, TF2A, and TF1 are respective illustrated in FIGS. 11A to 11D; importing the data into SIMCA software, standardizing the data and performing unsupervised principal component analysis, which makes the classification result more objective without pre-classification, and principal component analysis result of Sichuan Leshan black tea is illustrated in FIG. 7; then, carrying out supervised partial least squares discriminant analysis, obtaining rather accurate results by enlarging the differences between groups and reducing the differences within groups, and obtaining relevant data such as contribution rate and predictive ability, with the cumulative predictive ability (Q2) and cumulative variance contribution rate (R2Y) close to 1.0 indicating a good model, and the partial least squares discriminant analysis result of Sichuan Leshan black tea is illustrated in FIG. 8; further, carrying out hierarchical clustering analysis based on the partial least squares discriminant analysis, wherein hierarchical clustering analysis is to classify subjects according to their properties, and the distance between the large and small properties is far and near; it can be seen directly that clustering analysis gives the re-classification charts of different grades and different kinds of black tea, and the hierarchical cluster analysis result of Sichuan Leshan black tea is illustrated in FIG. 9; finally, developing a tea grade discrimination model based on HPLC, wherein the VIP value in partial least squares discriminant analysis can be used to quantify the contribution of each variable to classification, with VIP value greater than 1 indicating that there are significant differences among different types and grades of black tea; the VIP value shows that theine, ECG, theobromine and EGCG can be used to classify Sichuan black tea into Special-grade, Grade I and Grade II, and the contents of EGC, EC, ECG, EGCG, TF1, TF2A, TF2B, TF3, theobromine and theine in different grades of Sichuan Leshan black tea are illustrated in FIG. 12C; the evaluation results of grade are consistent with those of GB/T23776-2009, which proves that the method for evaluating the grade of black tea is accurate and effective.

The data standardization of the multivariate analysis software, the unsupervised principal component analysis method and the algorithm of the partial least squares discriminant analysis are the same as those in Embodiment 1.

What is claimed is:

1. A method for black tea grade determination, comprising the following steps:
   (1) preparing high-performance liquid chromatography (HPLC) standard solutions of ten kinds of components with different concentrations according to a gradient, and plotting standard curves;
   (2) adding black tea powder samples of different known grades individually into boiling water at 95-100° C. for extraction, cooling to room temperature after the extraction, followed by centrifugation, and then performing filtration of a supernatant with a filter membrane with a pore size in a range of 0.20-0.25 micrometers (um) to obtain black tea sample solutions;
   (3) separating and identifying components of the black tea sample solutions of the known grades by HPLC, and measuring contents of the ten kinds of components by a peak area normalization method;
   (4) standardizing data of the contents of the ten kinds of components in the black tea sample solutions, then carrying out unsupervised principal component analysis, and subsequently carrying out supervised partial least square discriminant analysis;
   (5) carrying out hierarchical clustering analysis on the basis of partial least squares discriminant analysis to obtain re-classification charts of different grades of different kinds of black teas, and establishing a tea grade discrimination model based on HPLC; and
   (6) processing a black tea powder sample to be tested by step (2) and step (3) once to obtain data associated with the black tea powder sample to be tested, and importing the obtained data into the tea grade discrimination model in step (5) to determine a grade of the black tea to be tested;
   wherein the ten kinds of components include epigallocatechin, epicatechin, epigallocatechin gallate, epicatechin gallate, theaflavin, theaflavin-3-gallate, theaflavin-3'-gallate, theaflavin-bis-gallate, theobromine and theine.

2. The method according to claim 1, wherein during separating and identifying components of the black tea sample solutions of the known grades by HPLC, a mobile phase of HPLC separation is acetonitrile and ultrapure water, and a flow rate thereof is 0.6-1.0 mL/min.

3. The method according to claim 1, wherein the standardizing data of the contents of the ten kinds of components in the black tea sample solutions, then carrying out unsupervised principal component analysis specifically comprises:
   (1) setting up n numbers of samples and p numbers of indexes, obtaining a data matrix $X=(X_{ij})_{n\times p}$, $i=1, 2, \ldots, n$, $j=1, 2, \ldots, p$, $x_{ij}$ represents a $j^{th}$ index value of an $i^{th}$ sample;
   (2) performing standardized transformation of data with Z-score method: $Z_{ij}=(x_{ij}-\bar{x}_j)/S_j$;
   (3) finding a correlation matrix R of index data: $R=(r_{jk})_{p\times p}$, $j=1, 2, \ldots, k=1, 2, \ldots, p$; $r_{jk}$ is a correlation coefficient between the index j and the index k;
   (4) finding eigenvectors of eigenvalues of the correlation matrix R to determine principal components: obtaining p numbers of eigenvalues $\lambda_g$ ($g=1, 2, \ldots, p$) from a characteristic equation $|\lambda I_p-R|=0$, ranking $\lambda_1$ in order of magnitude as $\lambda_1 \geq \lambda_2 \geq \ldots \geq \lambda_p \geq 0$, wherein $\lambda_g$ is a variance of principal component and its magnitude describes a role of each principal component in describing an evaluated object; according to the characteristic equation, each of the eigenvalues corresponds to one of eigenvectors $L_g(L_g=lg_1, lg_2, \ldots, l_{gp})g=1, 2, \ldots, p$; index variables after the standardizing are transformed into the principal components as that: $F_g=l_{g1}Z_1+l_{g2}Z_2+\ldots+l_{gp}Z_p$ ($g=1, 2, \ldots, P$), where $F_1$ is called as a first principal component, $F_2$ is called as a second principal component, $\ldots$, $F_p$ is called as a $p^{th}$ principal component;

(5) calculating a variance contribution rate and determine a number of the principal components:

the number of the principal components is equal to a number of original indexes, and if there are more original indexes, it is more troublesome to conduct comprehensive evaluation, principal component analysis is to select as few K numbers of principal components (k<p) as possible for comprehensive evaluation, and at the same time, make lost information as little as possible.

4. The method according to claim 1, wherein an algorithm of the partial least squares discriminant analysis specifically comprises:

(1) modeling method: setting up n numbers of samples, with q numbers of dependent variables and p numbers of independent variables; forming data tables X and Y for the independent and dependent variables; using partial least squares regression to extract t and u from X and Y respectively, with t and u carrying as much information as possible about variances in their respective data tables, and t and u being correlated to a maximum extent possible; after a first component has been extracted, implementing the partial least squares regression for X on t and for Y on t, respectively; if the regression equation has reached a target accuracy, the algorithm terminates; otherwise, a second round of component extraction is performed using residual information from an interpretation of X by t and residual information from an interpretation of Y by t, and then being repeated until the target accuracy is achieved; if multiple components are eventually extracted for X, the partial least squares regression then is performed by imposing a regression of yk on these components of X, which is expressed as a regression equation of yk on original independent variables;

(2) marking a data matrix obtained by X after standardization as $E_0=(E_{01}, \ldots, E_{0p})n \times p$ and a matrix corresponding to Y as $F_0=(F_{01}, \ldots, F_{0q})n \times q$; noting that $t_1$ is a first component of $E_0$, $t_1=E_{0w1}$, $w_1$ is a first axis of $E_0$ and is a unit vector, i.e. $\|w_1\|=1$; marking $u_1$ as a first component of $F_0$, $u_1=F_{0c1}$, $c_1$ is a first axis of $F_0$, and $\|c_1\|=1$; then, solving a following optimization problem, i.e., noting that $\theta_1=w_1'E_0'F_{0c1}$, which is precisely a objective function value of the optimization problem; using Lagrange algorithm, obtaining $E_0'F_0F_0'E_{0w1}=\theta_{12w1}$ and $F_0'E_0E_0'F_{0c1}=\theta_{12c1}$; therefore, $w_1$ is a unit eigenvector corresponding to a maximum eigenvalue of $E_0'F_0F_0'E_0$ matrix, and $c_1$ is a unit eigenvector corresponding to a maximum eigenvalue $\theta_{12}$ of $F_0'E_0E_0'F_0$ matrix; components $t_1=E_{0w1}$ and $u_1=F_{0c1}$ are obtained after finding the axes $w_1$ and $c_1$; then, finding regression equations: $E_0=t_1p_1'+E_1$, $F_0=t_{1r1}'+F_1$ of $E_0$ and $F_0$ on $t_1$ respectively, where regression coefficient vectors are $p_1=E_0't_1/\|t_1\|_2$, $r_1=F_0't_1/\|t_1\|_2$; and $E_1$ and $F_1$ are residual matrices of the two regression equations respectively; and (3) replacing $E_0$ and $F_0$ with the residual matrices $E_1$ and $F_1$, and then finding second axes $w_2$ and $c_2$ and second components $t_2$ and $u_2$, where $t_2=E_1w_2$, $u_2=F_1C_2$, $\theta_2=<t_2, u_2>=w_2'E_1'F_1C_2$; $w_2$ is a unit eigenvector corresponding to a maximum eigenvalue of $E_1F_1F_1'E_1$ matrix, while $c_2$ is a unit eigenvector corresponding to a maximum eigenvalue $\theta_{22}$ of $F_1'E_1E_1'F_1$ matrix; calculating regression coefficients $p_2=E_1't_2/\|t_2\|_2$, $r_2=F_1't_2/\|t_2\|_2$; therefore, there are regression equations: $E_1=t_2p_2'+E_2$, $F_1=t_2r_2'+F_2$; in this way, if a rank of X is A, then $E_0=t_1p_1'+\ldots+tA_{pA}'$; $F_0=t_1r_1'+\ldots+tArA'+FA$; and (4) cross-validity: one more component is worthwhile when a prediction error sum of squares in a case for one more component and one less sample divided by an error sum of squares in another case for one less component is less than 0.952, otherwise it is not worthwhile.

* * * * *